United States Patent [19]

Pearson et al.

[11] Patent Number: 5,512,053
[45] Date of Patent: Apr. 30, 1996

[54] SURGICAL SLEEVE AND TROCAR

[75] Inventors: Ronald W. Pearson, Denton; Steven S. Golden, Richardson; Kurt B. Spoonemore, Mansfield; Donald E. Exline, Carrollton; Carroll Hewitt, Dallas, all of Tex.

[73] Assignee: Dexide, Inc., Fort Worth, Tex.

[21] Appl. No.: 168,818

[22] Filed: Dec. 16, 1993

[51] Int. Cl.$^6$ ..................................................... A61M 5/00
[52] U.S. Cl. ..................... 604/167; 604/164; 604/264; 604/256
[58] Field of Search ................................. 604/164, 167, 604/264, 256, 104, 105

[56] References Cited

U.S. PATENT DOCUMENTS

| | | | |
|---|---|---|---|
| 4,112,932 | 9/1978 | Chiulli | 128/3 |
| 4,735,614 | 4/1988 | Yapp et al. | 604/165 |
| 5,122,122 | 6/1992 | Allgood | 604/174 |
| 5,201,714 | 4/1993 | Gentelia et al. | 604/167 |
| 5,211,633 | 5/1993 | Stouder, Jr. | 604/167 |
| 5,217,451 | 6/1993 | Freitas | 606/1 |
| 5,221,264 | 6/1993 | Wilk et al. | 604/167 |
| 5,224,930 | 7/1993 | Spacth et al. | 604/33 |
| 5,224,951 | 7/1993 | Freitas | 606/172 |
| 5,263,944 | 11/1993 | Vidal et al. | 604/256 |
| 5,290,249 | 3/1994 | Faster et al. | 604/167 |
| 5,300,036 | 4/1994 | Mueller et al. | 604/167 |
| 5,350,362 | 9/1994 | Stouder, Jr. | 604/167 |

OTHER PUBLICATIONS

Product Brochure, Origin Medsystems, Inc. ca. 1993 "Classic Tip Trocar".

Primary Examiner—John G. Weiss
Attorney, Agent, or Firm—Robert A. Felsman; Mark D. Perdue

[57] ABSTRACT

A surgical sleeve includes a housing and inner and outer sleeves coupled to the housing. A modular expandable hinge member is coupled to the outer sleeve and defines a radially expandable member to prevent inadvertent withdrawal of the surgical sleeve from a body cavity. A trigger is carried by the housing to cause relative movement between the inner and outer sleeves and radial expansion of the expandable member. The housing is further provided with a transversely slidable reducer assembly having three outer diameter seals for sealing against the exterior of surgical instruments having a variety of outer diameters. A trocar is provided for use with the surgical sleeve that is modular in construction and includes a shaft member and a modular, tubular, metallic cutting portion. The cutting portion forms only a portion of the trocar spike and the length of the shaft member governs the overall length of the trocar.

10 Claims, 3 Drawing Sheets

SURGICAL SLEEVE AND TROCAR

BACKGROUND OF THE INVENTION

1. Field of the Invention

The present invention relates generally to surgical instruments, and more particularly to cannulas or sleeves employed in endoscopic surgery.

2. Background Information

Surgical sleeves or cannulas are conventionally used in endoscopic or laparoscopic surgery to facilitate passage of surgical instruments such as endoscopes, clip appliers, and the like into a body cavity, usually the abdominal cavity. The sleeve is inserted through an incision made in the abdominal wall and into the body cavity, where it remains until the surgery is concluded. Various surgical instruments then are passed through the sleeve and into the body cavity to accomplish surgical procedures. Often, the body cavity is insufflated with an inert gas, such as $CO_2$, to lift the abdominal wall to facilitate viewing of the interior of the body cavity with the endoscope.

A recent improvement to these surgical sleeves is to provide the sleeve with an expandable member that is selectively expanded within the body cavity to prevent inadvertent full or partial withdrawal of the sleeve from the body cavity. Such surgical sleeves are disclosed in commonly assigned U.S. Pat. Nos. 5,122,122 and 5,217,451. The sleeves disclosed in those patents employ an expandable member in the form of an expandable hinge formed by a plurality of longitudinal slits made in the outer sleeve. Relative movement between inner and outer sleeves causes the expandable hinge structure to expand radially, wherein the sleeve resists withdrawal from the body cavity.

As presently manufactured, the expandable hinge structure is formed integrally with the outer sleeve portion of the sleeve assembly. Because the outer sleeve portion is generally tubular and several inches long, such sleeves are rather cumbersome and expensive to manufacture.

Surgical sleeves such as those in disclosed in U.S. Pat. Nos. 5,122,122 and 5,217,451 are used with surgical instruments of varying diameter. Typically, the sleeve is chosen to have an interior diameter large enough to accommodate the largest diameter instrument to be used with the sleeve. The sleeves are provided with seals that obstruct the inner diameter of the sleeve to prevent escape of insufflation gas from the body cavity, whether an instrument is present in the sleeve or not. Such seals typically include a lip seal for the sealing the interior passage of the sleeve when an instrument is not present in the sleeve, and an outer diameter (O.D.) seal to seal against the outer diameter of an instrument present in the sleeve. By necessity, the O.D. seal can only seal against instruments having outer diameters within a relatively small range, e.g., the O.D. seal in an 11 mm sleeve can seal against instruments having outer diameters between about 10 and 11 mm, but not against instruments much smaller than 10 mm in diameter. If a smaller diameter instrument is to be used with a sleeve, an auxiliary O.D. seal must me employed. These auxiliary O.D. seals are commonly known as "reducers," and as relatively small and separate parts, are clumsy in operation and represent one more item for operating room personnel to account for during surgical procedures.

A trocar or obturator is commonly used with a surgical sleeve to form the incision through which the sleeve is inserted into the body cavity. A trocar generally is a sharpened, pointed instrument that is placed in the surgical sleeve with the sharpened, pointed end protruding therefrom. The sleeve and trocar together are pressed against the exterior of the abdomen and the pointed end of the trocar forms the incision through which the sleeve is inserted. One such trocar is disclosed in commonly assigned U.S. Pat. No. 5,224,951. That trocar generally comprises a tubular, metallic sleeve having a sharpened and pointed end and a coring prevention means disposed in the sharpened end to prevent coring of tissue. Such a design is costly to manufacture because it requires that the cylindrical outer member, which extends the length of the trocar, be formed entirely of expensive surgical stainless steel.

A need exists, therefore, for a surgical sleeve and trocar that are modular in construction and thus less costly to manufacture. Additionally, a need exists for a surgical sleeve provided with an integral reducer capable of sealing against surgical instruments having a variety of outer diameters.

SUMMARY OF THE INVENTION

It is a general object of the present invention to provide an improved surgical sleeve and trocar for use in endoscopic surgical procedures.

These and other objects are accomplished by providing a surgical sleeve including a housing and inner and outer sleeves coupled to the housing. A modular expandable hinge member is coupled to the outer sleeve and defines a radially expandable member to prevent inadvertent withdrawal of the surgical sleeve from a body cavity. A trigger is carried by the housing to cause relative movement between the inner and outer sleeves and radial expansion of the expandable member. The housing is further provided with a transversely slidable reducer assembly having three outer diameter seals for sealing against the exterior of surgical instruments having a variety of outer diameters. A trocar is provided for use with the surgical sleeve that is modular in construction and includes a shaft member and a modular, tubular, metallic cutting portion. The cutting portion forms only a portion of the trocar spike and the length of the shaft member governs the overall length of the trocar.

Other objects, features and advantages of the present invention will become apparent with reference to the detailed description, which follows.

DESCRIPTION OF THE PREFERRED EMBODIMENT

Figure 1:
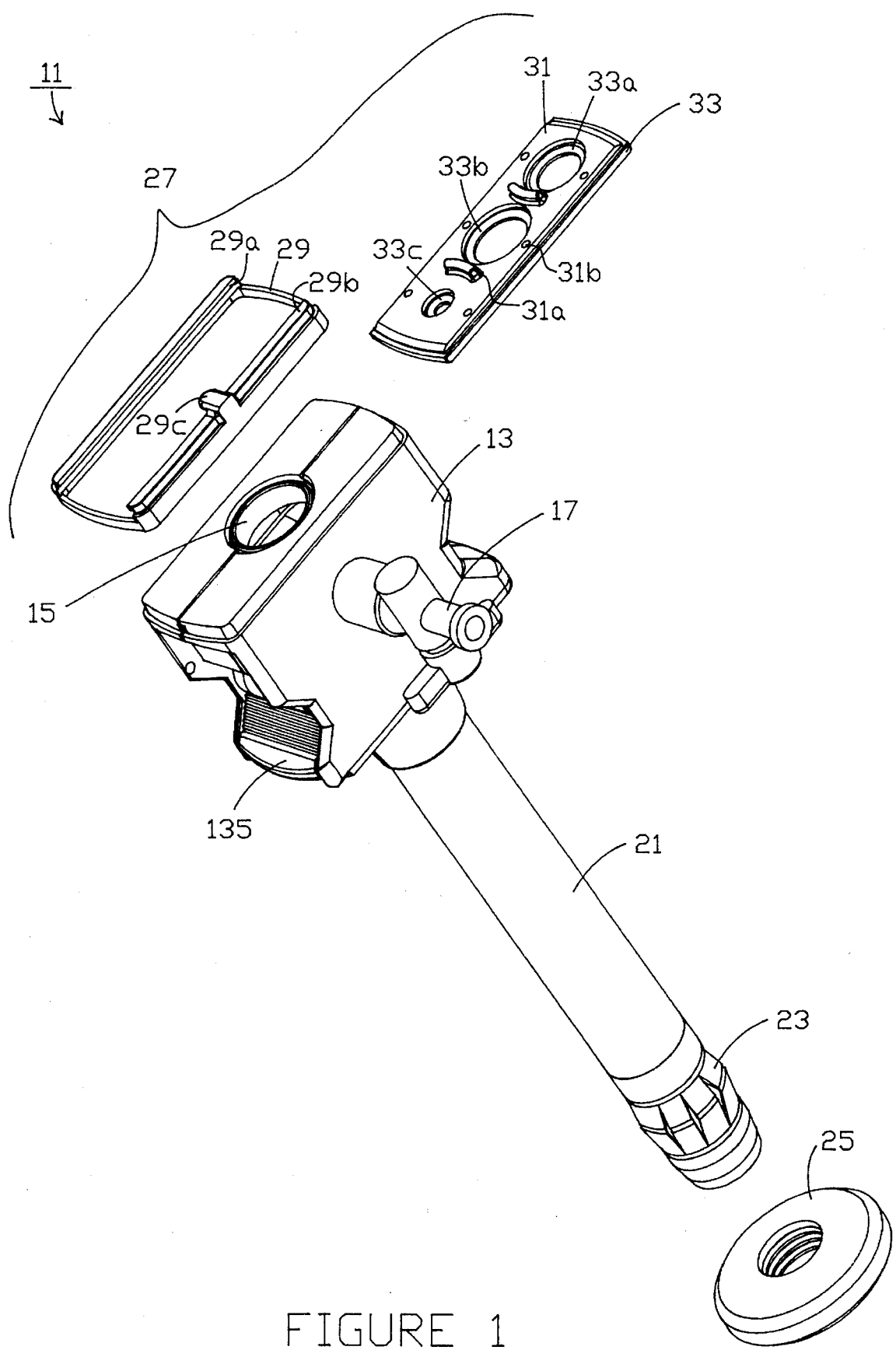
FIG. 1 is a perspective view of a surgical sleeve according to the present invention.

Referring now to FIG. 1, a surgical sleeve 11 according to the present invention is depicted. Surgical sleeve 11 comprises a housing 13, which is provided with an opening 15 at its upper end for introduction of surgical instruments (not shown) into sleeve 11. Housing 13 is further provided with a Luer fitting and stopcock 17 for attachment of a fluid pressure source (not shown) to supply insufflation gas through sleeve 11 to the body cavity (not shown) in which sleeve 11 is inserted. Housing 13 is further provided with a trigger 19 for actuation of the expandable means carried by sleeve 11.

A sleeve portion 21 is coupled to housing 13 and terminates in a modular expandable member 23. Manipulation of trigger 19 selectively causes radial expansion of modular expandable member 23 (as will be more fully described with reference to FIG. 2) to resist withdrawal of sleeve 11 from the body cavity in which it is inserted. A generally disk-like rubber stop member 25 is slidably carried on the exterior of sleeve portion 21. Stop member 25 is adapted to be moved against the exterior of the abdomen (not shown) to cooperate with expandable member 23 in immobilizing and sealing sleeve 11 in the body cavity. A transversely slidable reducer assembly 27 is disposed at the upper end of housing 13. Reducer assembly 27 comprises a frame 29, which is secured to housing 13 over opening 15. Frame 29 includes a pair of grooves 29a, 29b for slidably receiving a rigid slider plate 31. A layer 33 of resilient seal material, preferably formed of silicone rubber, is bonded to and generally coextensive with slider plate 31 and forms a fluid-tight seal between a portion of a snap cap (41 in FIG. 2) and slider plate 31 with slider plate 31 received in grooves 29a, 29b of frame 29. Slider plate 31 is provided with a pair of protrusions 31a, to facilitate manipulation of reducer assembly 27. Additionally, three pair of detent protrusions 31b on slider plate 31 cooperate with detent lip 29c on frame 29 to releasably position slider plate 31 within frame 29.

Slider plate 31 and resilient seal layer 33 are provided with three apertures 33a, 33b, 33c, which function as outer diameter seals to seal against the exterior of surgical instruments of varying diameters that are inserted into the body cavity through sleeve 11. Preferably, for a sleeve 11 having a nominal inner diameter of 12 mm, the apertures include an 10.5 mm aperture, a 8.1 mm aperture, and a 3.1 mm aperture (all dimensions are nominal). Provision of sliding reducer assembly 27 with these three apertures 33a, 33b, 33c, provides sleeve 11 with three O.D. seals to seal against the outer diameters of a variety of surgical instruments, wherein loss of insufflation gas through sleeve 11 is minimized. Additionally, because slider plate 31 is removably retained in frame 29 by detent members 29c, 31b, slider plate 31 can be removed and replaced with another slider plate having three different O.D. seals, further increasing the versatility of the present invention.

Figure 2:
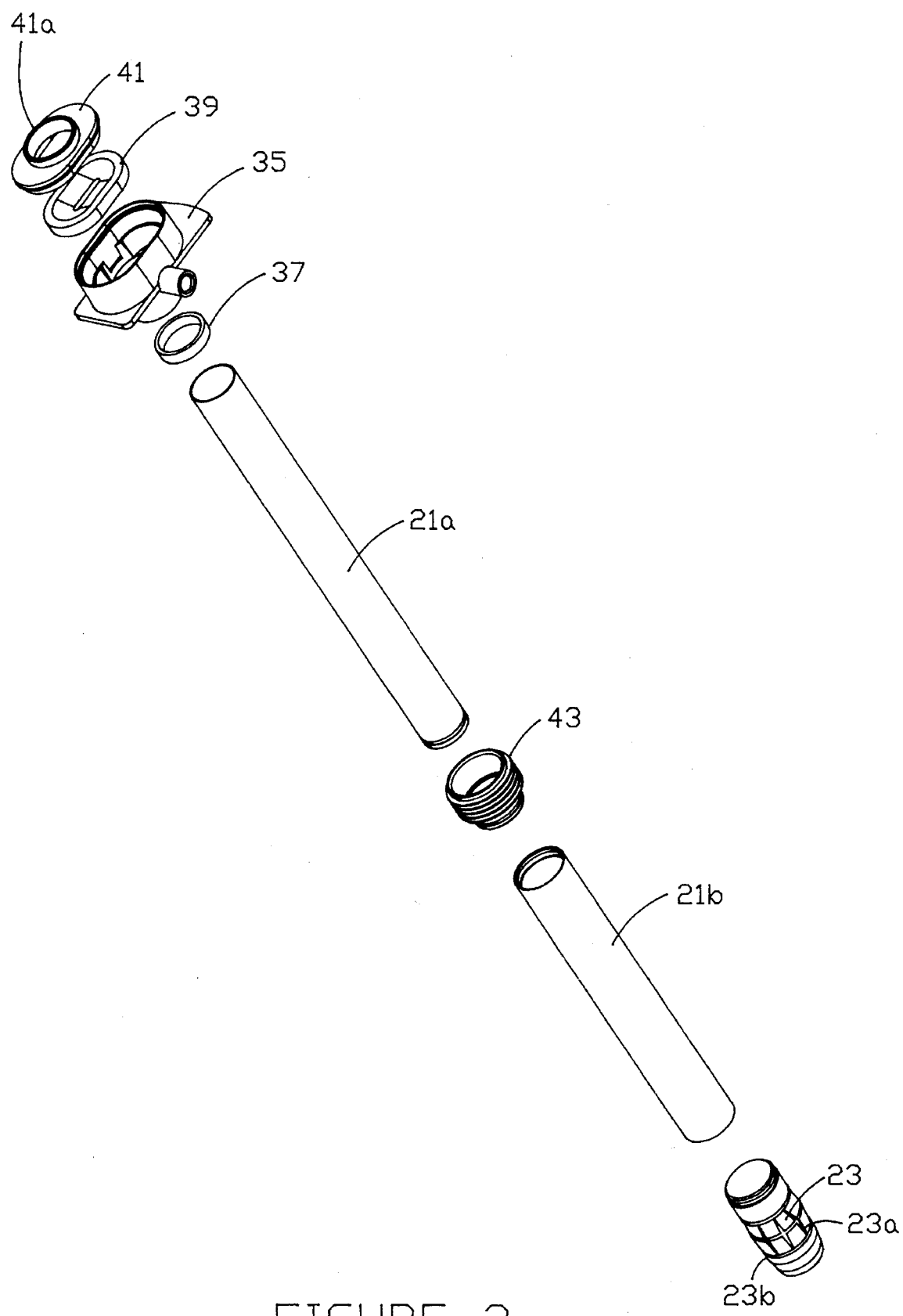
FIG. 2 is an exploded view of a portion of the surgical sleeve of FIG. 1.

FIG. 2 is an exploded view of various internal components of sleeve 11 illustrated in FIG. 1. Sleeve portion (21 in FIG. 1) comprises an inner sleeve 21a concentrically and slidably disposed within an outer sleeve 21b. Inner sleeve 21a is formed of fiberglass for strength and structural integrity. Modular expandable member 23 is coupled to a groove in the lowermost end of inner sleeve 21a. The uppermost end of modular expandable member 23 is coupled to the lowermost end of outer sleeve 21b. Modular expandable member 23 is generally cylindrical in configuration and includes a plurality of longitudinal slits 23a spaced around its circumference. The overall length of sleeve 11 may be varied simply by providing inner and outer sleeves 21a, 21b of varying length because modular expandable member 23 is separate from sleeves 21a, 21b. Relative movement between inner and outer sleeves 21a, 21b compresses modular expandable member 23 and causes the hinge members defined between longitudinal slits 23a to expand radially outwardly relative to the exterior of outer sleeve 21b. Three circumferential grooves 23b facilitate the expansion of the hinge members defined by longitudinal slits 23a.

A gear rack 43 is secured to the upper end of outer sleeve 21b and engages gear teeth (not shown) on trigger 19 to cause selective relative movement between sleeves 21a, 21b and the resulting expansion or contraction of expandable member 23. The uppermost end of inner sleeve 21a is secured to a body 35. A resilient seal ring 37, preferably formed of high-density foam, is provided between inner sleeve 21a and outer sleeve 21b to seal the space between the sleeves against leakage of insufflation gas through sleeve 11.

A lip seal 39, preferably formed of silicone rubber, is confined in body 35 by a snap cap 41. After housing 13 is assembled over body 35, an upwardly extending portion 41a of snap cap 41 extends through opening 15 in housing 13 to engage and seal against layer of seal material 33 of slidable reducer assembly 27. Lip seal 39 serves to seal sleeve 11 against escape of insufflation gas through sleeve 11 when no surgical instrument is present in sleeve 11. Thus, lip seal 39 and seal ring 37 between inner tube 21a and body 35 cooperate to render sleeve 11 fluid-tight when no surgical instrument is present therein. The multiple O.D. seals provided by sliding reducer assembly (27 in FIG. 1) seal against the outer diameters of surgical instruments present in sleeve 11 and extending through lip seal 39 to prevent escape of insufflation gas around the surgical instruments.

The detailed structure and operation of expandable member 23, lip seal 39, stop member 25, and trigger 19 are disclosed in commonly assigned U.S. Pat. Nos. 5,122,122 and 5,217,451.

Figure 3:
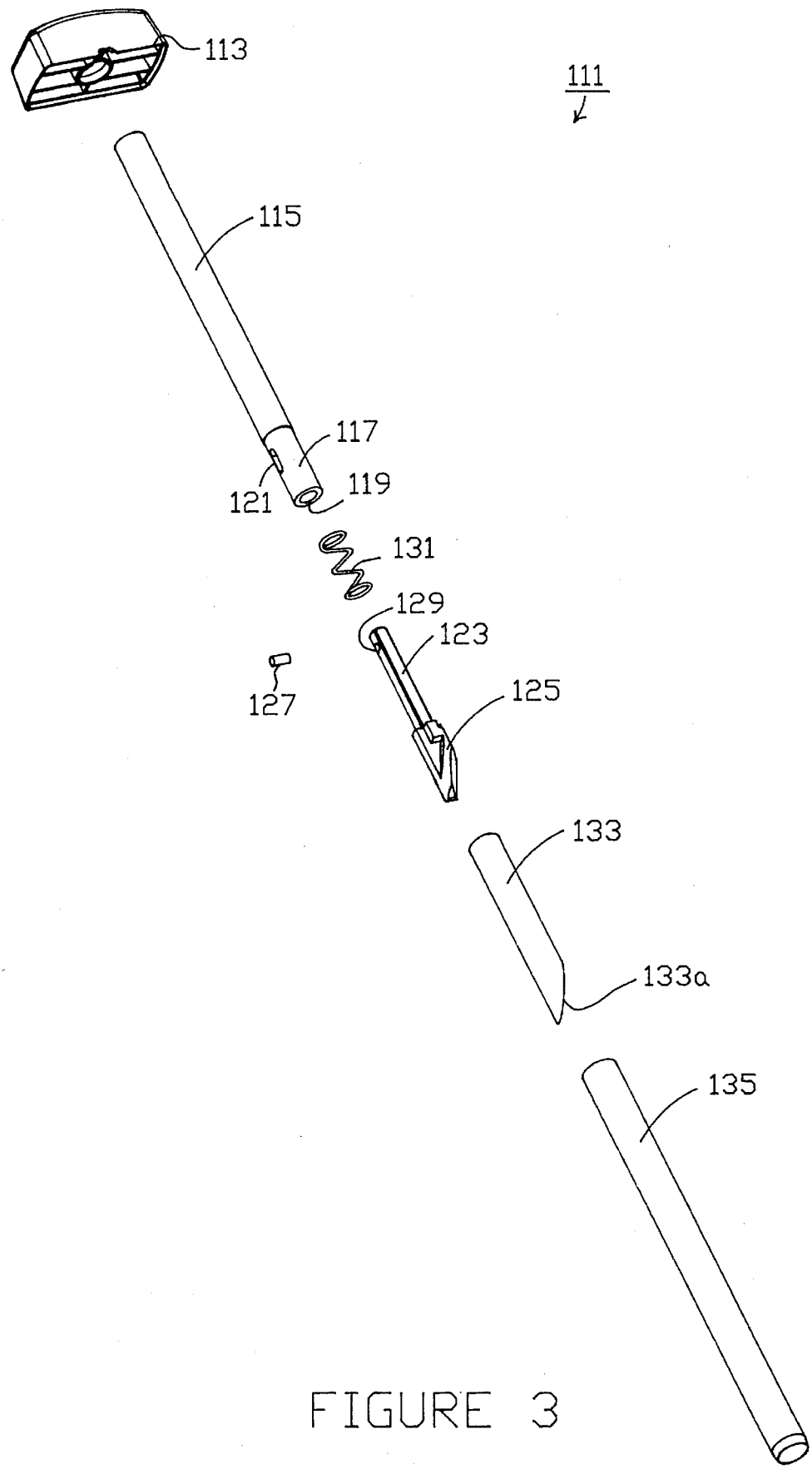
FIG. 3 is an exploded view of a trocar spike or obturator according to the present invention.

FIG. 3 illustrates a trocar spike or obturator 111 for use with the sleeve according to the present invention. Trocar spike or obturator 111 is employed with sleeve 11 to form the incision in the abdominal wall thorough which sleeve 11 is inserted into the body cavity.

Trocar spike 111 comprises a handle 113, which is secured to a shaft 115. Shaft 115 is formed of an inexpensive and easily manufactured plastic. A lower end portion 117 of shaft 115 is radially reduced to accommodate other portions of trocar spike 111. A passage 119 is formed in lower end 117 of shaft 115 and intersects a longitudinally extending slot 121 formed in shaft 115.

Passage 119 slidably receives a tongue portion 123 of a coring prevention member 125. A dowel pin 127 is received in an aperture 129 in tongue portion 123 of coring prevention member 125. Dowel pin 127 registers with longitudinal slot 121 in shaft 115 to prevent rotation of coring prevention member 125 relative to shaft 115 while permitting coring prevention member 125 to reciprocate longitudinally relative to shaft 115. A coil spring 131 is carried between coring prevention member 125 and shaft 115 and serves to bias coring prevention member 125 normally away from shaft 115.

A modular, tubular metallic cutting portion 133 is concentrically disposed over lowermost end 117 of shaft 115, coring prevention member 125, and spring 131. Cutting portion 133 is formed of surgical stainless steel and is angularly truncated and sharpened at its terminal end to define a tissue penetrating point 133a. Coring prevention member 125 is concentric with the interior of cutting portion 133 and serves to prevent coring of tissue as trocar spike 111 forms an incision, substantially as is disclosed in commonly assigned U.S. Pat. No. 5,224,951. Because cutting portion 133 is separate from the remainder of trocar 111 it can be manufactured separately from other components, and the other components can be manufactured of materials having lower cost than stainless steel. Moreover, the overall length of trocar 111 may be varied simply by varying the length of shaft 115. An outer sleeve 135 is disposed concentrically over shaft 115 and cutting portion 133 to provide a smooth and continuous exterior of trocar spike 111.

Unless otherwise indicated, all components of sleeve 11 and trocar spike 111 are formed of conventional plastics, including polypropylene, ABS, and glass-filled nylon. Sleeve 11 and trocar spike thus are designed to be disposable, single-use products.

In operation, trocar spike 111 is inserted into surgical sleeve 11 through opening 15 and tissue penetrating point 133a protrudes from the lowermost end of sleeve 11. Tissue penetrating point 133a of trocar 111 then is pressed against the abdomen of a patient, forming an incision through which trocar 111 and sleeve 11 are inserted into the abdominal cavity of the patient. After at least modular expandable portion 23 of sleeve 11 is inserted into the body cavity, trigger 19 is manipulated to cause relative movement between inner and outer sleeves 21a, 21b and radial expansion of modular expandable member 23. Inadvertent withdrawal of sleeve 11 from the body cavity is thus prevented. Stop member 25 is slid along exterior of sleeve portion 21 of sleeve 11 into abutment with the abdomen of the patient, thus immobilizing sleeve 11 within the body cavity. Stop member 25 and expandable member 23 cooperate to compress tissue around sleeve 11 and effectively seal sleeve 11 within the incision.

If desired, a fluid pressure source may be connected to Luer fitting and stopcock 17 to provide insufflation gas to the abdominal cavity to lift the abdominal wall and facilitate viewing of the body cavity. Trocar spike 111 then may be withdrawn from sleeve, wherein lip seal 39 prevents escape of insufflation gas through sleeve 11.

An endoscope (not shown) or other surgical instrument may be passed through sleeve 11 and into the body cavity to perform surgical procedures. As smaller diameter instruments are passed through sleeve 11, slidable reducer assembly 27 is manipulated to provide an appropriately dimensioned O.D. seal to seal against the exterior of the instrument to prevent loss of insufflation gas. Specifically, slider plate 31 is moved transversely relative to frame 29 and housing 13 to align the appropriate O.D. seal, defined by apertures 33a, 33b, 33c, with opening 15 in sleeve 11. Detents 29c, 31b releasably secure slider plate 31 and the O.D. seal in alignment with opening 15, and indicate to the user whether the O.D. seals are appropriately aligned with opening 15.

At the conclusion of surgical procedures, trigger 19 is manipulated to move modular expandable member 23 from the radially expanded state to a radially contracted state. Sleeve 11 then is withdrawn from the incision and the incision is closed.

The present invention has a number of advantages. The sliding reducer assembly provides a reducer that is integral with the remainder of the sleeve. This permits a single sleeve to be used with a wide variety of surgical instruments of varying diameter while preventing loss of insufflation gas between the surgical instrument and the sleeve. The sliding reducer assembly is not separate from the sleeve, and thus need not be separately accounted for during surgical procedures. The modular construction of the surgical sleeve and trocar spike separates expensive or difficult to manufacture portions from the remainder of the assembly and thus facilitates manufacturing. Furthermore, the modular designs permit the overall length of the sleeve and trocar spike to be varied simply by varying the length of the inner and outer sleeves of the sleeve and the shaft of the trocar spike.

The invention has been disclosed with reference to a preferred embodiments thereof. It will be apparent to those skilled in the art that the invention is thus not limited but is susceptible to variation and modification without departing from the scope and spirit thereof.

We claim:

1. A surgical sleeve for the introduction of surgical instruments into a body cavity, the surgical sleeve comprising:

a housing having an opening through which surgical instruments are introduced into the sleeve;

a sleeve portion extending from the housing; and a reducer assembly including:

a rigid slider plate slidably and removeably coupled to the housing;

a resilient, laminar seal layer generally coextensive with the slider plate and disposed between the slider plate and the housing and sealingly engaging a portion of the housing; and a plurality of apertures formed in the slider plate and the seal layer, the apertures having varying diameters and defining seals that are selectively movable over the opening in the housing to seal against exteriors of instruments disposed in the sleeve.

2. The surgical sleeve of claim 1 further including a seal member disposed in the surgical sleeve to seal against escape of gas from the body cavity with no surgical instrument in the sleeve.

3. The surgical sleeve of claim 1 further comprising:

at least one detent disposed between the housing and the slider plate to releasably secure the slider plate in a position in which one of the apertures is disposed over the opening in the housing.

4. The surgical sleeve of claim 1 further comprising:

a pair of rails carried by the housing for engagement with the edges of the slider plate to slidably and removeably couple the slider plate to the housing.

5. The surgical sleeve of claim 1 wherein the seal layer is secured to the slider plate.

6. A surgical sleeve for the introduction of surgical instruments into a body cavity, the surgical sleeve comprising:

a housing having an opening through which surgical instruments are introduced into the sleeve;

a sleeve portion extending from the housing, the sleeve portion including an outer sleeve and an inner sleeve concentrically disposed in the outer sleeve;

an expandable member carried by the sleeve portion to selectively radially expand to resist withdrawal of the sleeve from the body cavity; and a reducer assembly including:

a rigid slider plate slidably and removeably coupled to the housing by a pair of grooves carried by the housing;

a resilient, laminar seal layer generally coextensive with the slider plate and disposed between the slider plate and the housing and sealingly engaging a portion of the housing; and a plurality of apertures formed in the slider plate and the seal layer, the apertures having varying diameters and defining seals that are selectively movable over the opening in the housing to seal against exteriors of instruments disposed in the sleeve.

7. The surgical sleeve of claim 6, further comprising:

at least one detent disposed between the housing and the slider plate to releasably secure the slider plate in a position in which one of the apertures is disposed over the opening in the housing.

8. The surgical sleeve of claim 6 wherein the seal layer is secured to the slider plate.

9. A surgical sleeve for the introduction of surgical instruments into a body cavity, the surgical sleeve comprising:
   a housing having an opening through which surgical instruments are introduced into the sleeve;
   a sleeve portion extending from the housing; and
   a reducer assembly including:
      a slider plate slidably and removeably coupled to the housing;
      a resilient seal layer disposed between the slider plate and the housing and sealingly engaging a portion of the housing;
      a plurality of apertures formed in the slider plate and the seal layer, the apertures having varying diameters and defining seals that are selectively movable over the opening in the housing to seal against exteriors of instruments disposed in the sleeve; and
      at least one detent disposed between the housing and the slider plate to releasably secure the slider plate in a position in which one of the apertures is disposed over the opening in the housing.

10. The surgical sleeve of claim 9 further including a seal member disposed in the surgical sleeve to seal against escape of gas from the body cavity with no surgical instrument in the sleeve.

* * * * *